(12) United States Patent
Jeon

(10) Patent No.: US 9,717,944 B2
(45) Date of Patent: Aug. 1, 2017

(54) HEALTH PROMOTION SYSTEM USING WIRELESS AND ROPELESS JUMP ROPE APPARATUS

(71) Applicant: Famspo Co. Ltd., Seoul (KR)

(72) Inventor: Bong Sam Jeon, Seoul (KR)

(73) Assignee: FAMSPO CO. LTD., Seoul (KR)

( * ) Notice: Subject to any disclaimer, the term of this patent is extended or adjusted under 35 U.S.C. 154(b) by 0 days.

(21) Appl. No.: 14/836,986

(22) Filed: Aug. 27, 2015

(65) Prior Publication Data

US 2016/0059073 A1    Mar. 3, 2016

(30) Foreign Application Priority Data

Aug. 29, 2014 (KR) .......................... 10-2014-0113763

(51) Int. Cl.
*A63B 71/00* (2006.01)
*A63B 21/00* (2006.01)
(Continued)

(52) U.S. Cl.
CPC ............ *A63B 21/4035* (2015.10); *A61B 5/11* (2013.01); *A63B 5/20* (2013.01); *A63B 21/4037* (2015.10); *G06F 19/3481* (2013.01); *G06K 9/00342* (2013.01); *G06Q 30/0241* (2013.01); *G06Q 50/20* (2013.01); *G09B 19/003* (2013.01);
(Continued)

(58) Field of Classification Search
CPC ... A63B 5/20; A63B 24/0062; A63B 24/0075; A63B 2024/0068; A63B 2024/0065; A63B 21/06; A63B 21/4035; G09B 19/003; A63F 2300/80; A63F 2300/8005;
(Continued)

(56) References Cited

U.S. PATENT DOCUMENTS 6,810,735 B2 * 11/2004 Kaneko .............. G01C 19/5607
  73/493
7,329,212 B2 * 2/2008 Roque .................... A63B 15/00
  482/110
(Continued)

FOREIGN PATENT DOCUMENTS

JP    2001346901 A    12/2001
KR    200335828 Y1    12/2003
(Continued)

*Primary Examiner* — Loan H Thanh
*Assistant Examiner* — Megan Anderson
(74) *Attorney, Agent, or Firm* — Mark M. Friedman

(57) ABSTRACT

There is provided a health promotion system using a wireless and ropeless jump rope. When a plurality of users use a plurality of wireless and ropeless jump rope apparatuses, each wireless and ropeless jump rope apparatus transmits each user's weight, the number of jumps made by the user and the time of using the wireless and ropeless jump rope to an external health promotion server. The health promotion server analyzes the user's weight, the number of jumps made by the user and the time of using the wireless and ropeless jump rope as transmitted and provides an instructor with the information of the number of jumps made by the user and the analyzed health-relevant data. The instructor who receives the information of the number of jumps made by the user and the analyzed health-relevant data is able to improve the health of the user.

8 Claims, 7 Drawing Sheets

(51) Int. Cl.
*A63B 5/20* (2006.01)
*G09B 19/00* (2006.01)
*A61B 5/11* (2006.01)
*G06F 19/00* (2011.01)
*G06K 9/00* (2006.01)
*G06Q 30/02* (2012.01)
*G06Q 50/20* (2012.01)
*A63B 24/00* (2006.01)
*A63B 71/06* (2006.01)

(52) U.S. Cl.
CPC ....... *A63B 24/0075* (2013.01); *A63B 71/0622* (2013.01); *A63B 2024/0068* (2013.01); *A63B 2071/063* (2013.01); *A63B 2071/065* (2013.01); *A63B 2071/0625* (2013.01); *A63B 2071/0627* (2013.01); *A63B 2220/10* (2013.01); *A63B 2220/16* (2013.01); *A63B 2220/17* (2013.01); *A63B 2220/18* (2013.01); *A63B 2220/34* (2013.01); *A63B 2220/44* (2013.01); *A63B 2220/56* (2013.01); *A63B 2220/801* (2013.01); *A63B 2220/805* (2013.01); *A63B 2225/20* (2013.01); *A63B 2225/50* (2013.01); *A63B 2225/54* (2013.01); *A63B 2230/01* (2013.01); *A63B 2230/75* (2013.01)

(58) Field of Classification Search
CPC ............ A63F 2300/8094; A63F 13/816; A63F 13/92; A63F 13/98
USPC ............................................. 73/493, 379.01
See application file for complete search history.

(56) References Cited

U.S. PATENT DOCUMENTS

| | | | | |
|---|---|---|---|---|
| 7,354,383 B2* | 4/2008 | Bardha | ................... | A63B 5/20 482/81 |
| 7,621,853 B2* | 11/2009 | LaTour | ................... | A63B 5/20 482/81 |
| 7,621,854 B2* | 11/2009 | Foxman | ................... | A63B 5/20 482/81 |
| 7,976,438 B1* | 7/2011 | Hsu | ......................... | A63B 5/20 482/81 |
| 8,009,866 B2* | 8/2011 | Ueshima | ................ | A63B 22/00 348/119 |
| 8,088,047 B2* | 1/2012 | Marji | ....................... | A63B 5/20 482/82 |
| 8,142,333 B2* | 3/2012 | LaTour | ................... | A63B 5/20 482/8 |
| 2004/0002408 A1* | 1/2004 | Rigas | ...................... | A63B 5/20 482/82 |
| 2006/0262120 A1* | 11/2006 | Rosenberg | ............. | G06F 3/011 345/473 |
| 2008/0215974 A1* | 9/2008 | Harrison | ................ | A63F 13/10 715/706 |
| 2010/0173756 A1* | 7/2010 | Lee | ........................... | A63B 5/20 482/81 |
| 2011/0130247 A1* | 6/2011 | Lovett | ..................... | A63B 5/20 482/3 |
| 2011/0169725 A1* | 7/2011 | Ueshima | .............. | A61B 5/1124 345/156 |
| 2011/0184248 A1* | 7/2011 | Furuta | .................. | A61B 5/0002 600/300 |
| 2011/0306474 A1* | 12/2011 | Gamboa | .................. | A63B 5/20 482/81 |
| 2013/0280684 A1* | 10/2013 | Gordon | ................... | A63B 5/20 434/247 |
| 2014/0038780 A1* | 2/2014 | Lin | .......................... | A63B 5/20 482/8 |

FOREIGN PATENT DOCUMENTS

KR 1020060037098 A 6/2007
KR 101132699 B1 4/2012

* cited by examiner

HEALTH PROMOTION SYSTEM USING WIRELESS AND ROPELESS JUMP ROPE APPARATUS

CROSS-REFERENCE TO RELATED APPLICATION

This application claims the benefit of Korean Patent Application No. 10-2014-0113763, filed on Aug. 29, 2014, the disclosure of which is hereby incorporated herein by reference in its entirety.

BACKGROUND OF THE INVENTION

1. Field of the Invention

The present invention relates to a health promotion system using a wireless jump rope apparatus, and more particularly, to a health promotion system using a wireless and ropeless jump rope, which is capable of counting the number of jumps a user of the wireless and ropeless jump rope makes, by using the output of a rotation sensing sensor positioned at handles and the output of a jump sensing sensor positioned at a mat.

2. Description of the Related Art

In general, a jump rope consists of a long rope extruded to be long using a flexible synthetic resin material and a pair of handles positioned at both ends of the rope. A user holding the handles by the hands rotates the rope over the body and simultaneously jumps over the rotating rope to pass before it touches the ground.

Since jumping rope is an exercise evenly using the whole body including the arms rotating the rope and the legs used upon jumping, ten (10) minutes of jumping rope obtains a sufficient exercise effect. Therefore, jumping rope is a popular exercise that men and women of all ages can easily enjoy.

Further, the characteristic of the exercise of jumping with the rope is a vertical exercise that the user jumps using the front parts of the feet. Since an intensive stimulus is applied to the ankles, calves, knees and waist, etc. whenever the user jumps for jumping rope, it is effective in strengthening the function of each part of the body. Since this stimulus has an effect on bone growing cells, it is known as stimulating the growth of an adolescent.

The exercise of jumping with the rope has merit that if a simple exercise device is available, a user can easily enjoy anytime. However, since a spacious space is needed to jump using a long rope, when the user jumps rope indoors, this may result in any damage to surrounding items or people. Moreover, when the user jumps rope, the rope touches the floor and therefore an impact noise occurs.

At present, the exercise of jumping the rope is periodically conducted in schools for the students' health. In this case, since one teacher administers the number of jumps each of many students makes by using a rope, the time of the jumping rope exercise of each student and the weight of each student, the learning of jumping rope or the weight control is not efficiently performed.

Furthermore, since the exercise of jumping the rope needs a large space, it is conducted in the playground of a school when the school has no indoor auditorium hall or indoor gym. However, when the exercise of jumping the rope is conducted in the playground, it is not good to students who are easily exposed to severe dust. Even though the exercise of jumping the rope is conducted in the school playground which is equipped with artificial turf or natural lawn, it is not easy to do the exercise of jumping the rope all year because of the weather conditions, such as snow or rain, and the environmental pollution problems, such as fine dust/yellow dust/toxic gas.

PRIOR ART DOCUMENT

Patent Document 1: Korean Patent No. 1132699

SUMMARY OF THE INVENTION

Therefore, it is an object of the present invention to solve the above m problems and to provide a health promotion system using a wireless and ropeless jump rope to accurately count the number of jumps a user of the wireless and ropeless jump rope makes, by using the output of a rotation sensing sensor positioned at handles and the output of a jump sensing sensor positioned at a mat.

Further, it is another object of the present invention to provide a health promotion system using the wireless and ropeless jump rope to provide a health promotion server with the number of jumps the user makes by using the wireless and ropeless jump rope of a wireless and ropeless jump rope apparatus, to manage the number of jumps the user makes, and to receive health-related data from the health promotion server.

In accordance with an embodiment of the present invention, there is provided a health promotion system using a wireless and ropeless jump rope comprising a wireless and ropeless jump rope apparatus with a handle unit and a floor mat unit, a health promotion server configured to communicate with the wireless and ropeless jump rope apparatus, and a user terminal to access the health promotion server. The handle unit comprises a pair of handle bodies, weights and strings each connecting the handle body and the weight, an acceleration sensor and an angular velocity sensor included in the weight as a rotation sensing sensor module to sense the rotation of the weight of each handle, an incline sensor further installed in an upper end of the handle body where the string is fixed, to detect an incline of the handle unit, and a handle communication module to transmit the output of the rotation sensing sensor module and the output of the incline sensor to the floor mat unit. The floor mat unit comprises a weight sensing sensor module to sense a use's weight when the user is positioned on the floor mat unit, a jump sensing sensor module to sense the user's jump(s) when the user jumps on the floor mat unit, a mat communication module to receive the output of the rotation sensing sensor module and the output of the incline sensor transmitted from the handle communication module, a mat controller to count the number of jumps made by the user of the wireless and ropeless jump rope, by using the outputs of the rotation sensing sensor module and incline sensor received through the mat communication module and the output of the jump sensing sensor module of the floor mat unit, and an external communication module to transmit the user's weight measured in the weight sensing sensor module and the number of the jumps counted in the mat controller. The health promotion server comprises a user database to store information including the individual user's height and weight provided when the user registers in the health promotion server, the user's weight, the number of jumps made by the user of the wireless and ropeless jump rope and the time of using the wireless and ropeless jump rope which are transmitted from the external communication module of the wireless and ropeless jump rope apparatus, a user analysis server to analyze information stored in the user data base and to store the analyzed data in the user database, a web-service serve, and an application service server to provide the data analyzed in the user analysis server through an application installed in the user terminal, wherein the user analysis server generates analysis data of the individual user's wireless and ropeless jump rope exercise, by using the height and weight information stored in the user database, the user's current weight, the number of jumps made by the user of the wireless and ropeless jump rope and the time of exercising using the wireless and ropeless jump rope as transmitted from the external communication module of the wireless and ropeless jump rope apparatus, and it provides the generated analysis data to the user terminal.

Further, the jump sensing sensor module may use any one of a tape switch mode, a bumper switch mode, a contact switch mode, an acceleration switch mode and a laser switch mode.

Further, the mat controller changes the wireless and ropeless jump rope apparatus from a sleep mode to a normal operation mode if the operation of the switch is sensed.

Further, the user analysis server provides health analysis data and recommended health data of the individual user, by using the height and weight information stored in the user database, the user's current weight, the number of jumps made by the user of the wireless and ropeless jump rope and the time of using the wireless and ropeless jump rope as transmitted from the wireless and ropeless jump rope apparatus.

Further, the application installed in the user terminal includes a student application and an instructor application, and if the application installed the user's application is the student application, the data analyzed in the user analysis server and provided to the user are analysis data of the wireless and ropeless jump rope exercise and if the application is the instructor application, the health analysis data and recommended health data in addition to the analysis data of the wireless and ropeless jump rope exercise are further provided.

Further, the analysis data of the wireless and ropeless jump rope exercise are a trend in the individual user's wireless and ropeless jump rope exercise from the past to the present, the amount of the exercise by day/month, the average number of successful jumps with the wireless and ropeless jump rope per use, the maximum number of successful jumps with the wireless and ropeless jump rope per use, the maximum duration of using the wireless and ropeless jump rope per use, the average/maximum/minimum number of jumps with the wireless and ropeless jump rope per minute, consumed calories per day/month, and the relevant statistical data on the wireless and ropeless jump rope exercise.

Further, the health analysis data includes the analysis data of the wireless and ropeless jump rope exercise, the data analyzing whether the user is overweight, low-weight or low-physical strength by comparing the individual user's height and weight information with the amount of the wireless and ropeless jump rope exercise, and evaluation data of the user's elements required for the wireless and ropeless jump rope exercise, such as endurance, reflex, etc.

Further, the recommended health data are the data relating to the recommended amount of exercise, recommended diet and recommended exercise which are customized for the individual user, to strengthen the weak element of the user on the basis of the health analysis data of the individual user.

EFFECTS OF THE INVENTION

According to the present invention, since the wireless and ropeless jump rope apparatus does not need any physical rope, using the wireless and ropeless jump rope can be conducted in a small-sized indoor area such as an empty classroom. Therefore, even in the school where there is no indoor gym or indoor auditorium hall, the exercise using the wireless and ropeless jump rope can be easily conducted without any outside weather influence (for example, snow, rain, yellow dust, fine dust and toxic gas).

According to the present invention, even if one teacher is in charge of a number of students, the teacher does not need to count the number of jumps each student makes from start to end. Therefore, the teacher can assign much more time to student guidance for using the wireless and ropeless jump rope. Furthermore, since the teacher can easily know the weight state, the change or development in exercising using the wireless and ropeless jump rope and whether overweight/low strength of each student, based on the analysis data (materials) provided from the health promotion server, a customized health promotion result for each student is possible.

According to the present invention, a data mining analysis and statistical analysis are possible without any time investment, based on the data of jumps each student makes by using the wireless and ropeless jump rope. Therefore, it is possible to encourage the wireless and ropeless jump rope exercise by offering an incentive (by providing a book gift, gift certificate or gift card) to a top-ranking school or student.

According to the present invention, the state of the physical strength of each student or the recommended amount of exercise and recommended diet information corresponding to the physical strength state are provided from the health promotion server to the teacher or parents. Therefore, the efficiency of the physical strength and health promotion of the student is improved.

BRIEF DESCRIPTION OF THE DRAWINGS

The above and other features and advantages of the present invention will become more apparent to those of ordinary skill in the art by describing in detail the preferred embodiments thereof with reference to the attached drawings in which:

FIG. 1b is a schematic internal constitution view of the wireless and ropeless jump rope apparatus shown in FIG. 1a;

FIG. 2a is a detailed view of the constitution provided in the handle unit shown in FIG. 1, showing an example wherein an acceleration sensor module is used as the rotation sensing sensor module;

Figure 1A:
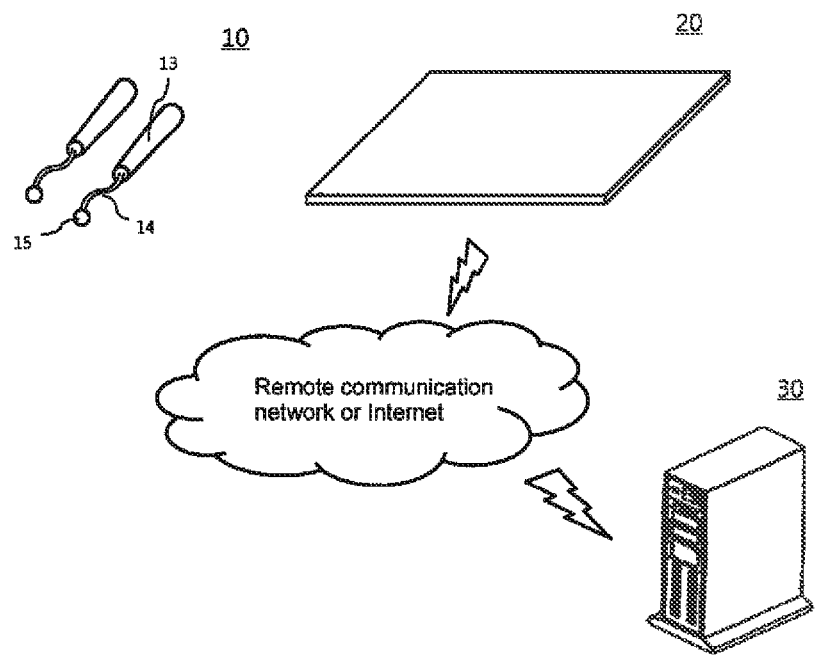
FIG. 1a is a schematic external constitution view of a wireless and ropeless jump rope apparatus of a health promotion system according to an embodiment of the present invention.

[Description of numbers for constituents in drawings]

| | |
|---|---|
| 10: handle unit | 11: rotation sensing sensor module |
| 12: handle communication module | 20: floor mat unit |
| 21: weight sensing sensor module | 22: jump sensing sensor module |
| 23: mat communication module | 24: external communication module |
| 25: display module | 26: sound module |
| 30: health promotion server | 31: user database |
| 32: user analysis server | 33: web-service server |
| 34: application service server | 40: user/instructor PC |
| 51: instructor application | 52: user application |

DETAILED DESCRIPTION OF THE PREFERRED EMBODIMENT

The embodiment(s) of the present invention is provided so that the disclosure of the present invention will be complete and will fully convey the scope of the invention to those skilled in the art to which this invention belongs. The present invention shall be defined by the scope of the claims. Therefore, well-known constituent elements, operations and techniques are not specifically described in some embodiments to prevent the present invention from being obscurely interpreted.

Throughout the application, the same reference numerals indicate the same constituent elements. The terms used (stated) herein are to explain the embodiment(s) and not to limit the present invention. The singular forms used herein are intended to include the plural forms as well, unless the context clearly indicates otherwise. The terms, such as "comprises", "comprise/comprising (or includes/including), specify the present of stated constitutional elements and operations but do not preclude the presence or addition of one or more other constitutional elements and operations.

Unless otherwise defined, all terms (including technical and scientific terms) used herein have the same meaning as commonly understood by one of ordinary skill in the art. Further, terms, such as those defined in commonly used dictionaries, will not be interpreted in an idealized or overly formal sense unless expressly so defined herein.

Hereinafter, the technical characteristics of the present invention will be described more fully with reference to the accompanying drawings.

Since a general explanation of a wireless and ropeless jump rope described in Korean Patent No. 1132699 as mentioned above is of help in understanding the present invention, its preamble is included in the present invention.

FIG. 1 is a block diagram of the schematic constitution of a health promotion system with a wireless and ropeless jump rope apparatus according to an embodiment of the present invention.

Figure 1B:
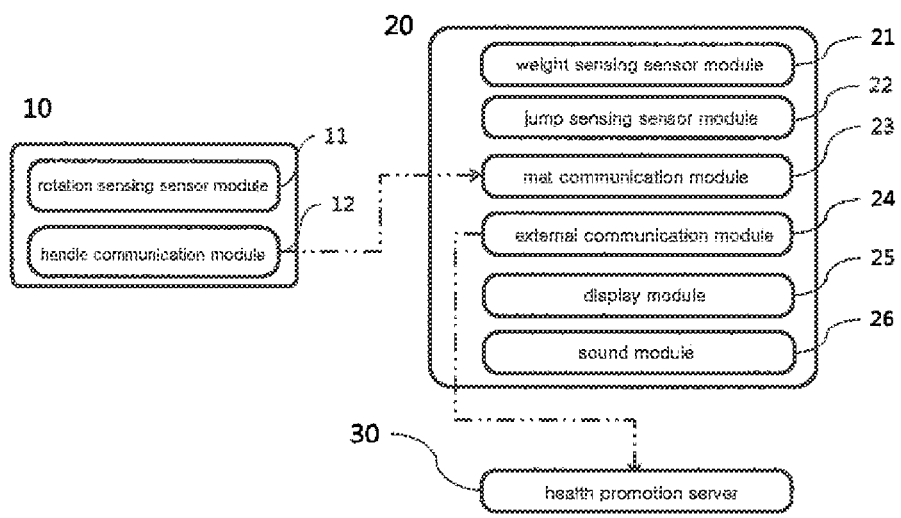

As shown in FIG. 1a and FIG. 1b, the health promotion system comprises a wireless and ropeless jump rope apparatus and a health promotion server 30. The wireless and ropeless jump rope apparatus comprises a handle unit 10 and a floor mat unit 20.

The wireless and ropeless jump rope apparatus according to the present invention will be described in more detail. As shown in FIG. 1a, the handle unit 10 of the wireless and ropeless jump rope apparatus includes a pair of cylindrical handle bodies 13 each having the same shape and weights 15 each connected to each handle body 13 through a connecting string 14. The cylindrical handle body 13 may include a handle communication module 12 for the communication with the floor mat unit 20. The weight 15 may be selected within the range of a proper weight in consideration of a user. The weight 15 may be hollow in which a rotation sensing sensor module 11 is installed.

FIG. 1b is a block diagram schematically illustrating the electronic devices included in the handle unit 10 and the floor mat unit 20 of the wireless and ropeless jump rope apparatus. The handle unit 10 includes the rotation sensing sensor module 11 to sense the rotation of the handle unit 10 by the user, and the handle communication module 12 to transmit data from the rotation sensing sensor module 11 to the floor mat unit 20.

Specifically, the rotation sensing sensor module 11 of the handle unit 10 is installed in at least any one of the handle bodies 13. Preferably, the rotation sensing sensor module 11 comprises any one of an acceleration sensor module, an angular velocity sensor module and a photo interrupt sensor module or a combination thereof, to sense a movement of the handle unit 10 in a three-dimensional space. The handle communication module 12 is to wirelessly transmit an output of the acceleration sensor module to the floor mat unit 20. In the embodiment, the handle communication module 12 uses Bluetooth but the present invention is not limited thereto. It may use a local area communication module, such as Zigbee.

The floor mat unit 20 of the wireless and ropeless jump rope apparatus includes a floor mat (not shown) making it possible to jump using the wireless and ropeless jump rope. It also may include an absorption pad (not shown) preventing or lessening impact and noise on the floor mat. Preferably, the absorption pad is made of a polyurethane material.

Specifically, the floor mat unit 20 comprises a weight sensing sensor module 21 to measure the weight of the user, a jump sensing sensor module 22 to sense the jumps of the user, a mat communication module 23 to wirelessly receive the output of the rotation sensing sensor module 11 from the handle communication module 12, an external communication unit 24 to communicate with the health promotion server 30 positioned at the external network, a display module 25 to display simple information, such as the weight and the number of jumps with the wireless and ropeless jump rope, to the user, and a sound module 26 to provide the user with a simple guide voice or a warning sound.

The weight sensing sensor module 21 performs a first measurement when the user positioned on the mat to jump by using the wireless and ropeless jump rope. The measured weight is displayed to the user through the display module 25 and simultaneously is transmitted to the health promotion server 30 through the external communication module 24 included in the floor mat unit 20, to be recorded and saved by individual.

The jump sensing sensor module 22 detects the jumps of the user on the floor mat unit 20. A control unit 348 of the mat communication module 23 is configured to count the number of jumps made by the user of the wireless and ropeless jump rope, by synchronizing the output of the rotation sensing sensor module 11 transmitted from the handle communication module 12 and the output of the jump sensing sensor module 23.

The external communication module 24 is configured to transmit the value of counting the number of jumps the user of the wireless and ropeless jump rope makes and the time of using the wireless and ropeless jump rope measured in the mat communication module 23 to the health promotion server 30 positioned at the external network. Although the external communication module 24 may use any one of a wire communication module and wireless communication module compatible with Ethernet, the embodiment uses a wireless communication module using Wi-Fi for the mobility and convenience of the wireless and ropeless jump rope apparatus.

The display module 25 displays the weight of the user when the user positions on the floor mat unit 30 to jump using the wireless and ropeless jump rope. The display module 25 also functions as a visual guide unit to display the number of jumps the user of the wireless and ropeless jump rope makes on an LCD of the display module 25. The sound module 26 is an audio guide unit to provide a pre-saved simple precaution or guide comment or a start alarm sound before the user starts a wireless and ropeless jump rope exercise or to provide an end alarm or an end guide after the user finishes the wireless and ropeless jump rope exercise. Of course, the user's weight or the number of jumps the user of the wireless and ropeless jump rope makes can be informed to the user through the sound module 26. However, depending on the users, since such information is related to an individual privacy that the user is reluctant to let others know, it is more desirable to distinguish the display module for the individual privacy from the sound module for the common information guidance.

The health promotion server 30 is positioned at the external network to manage the weight value and the number of jumps of the user, which are received from the wireless and ropeless jump rope apparatus. The health promotion server 30 will be more specifically described in the health promotion system according to the present invention.

Figure 2A:
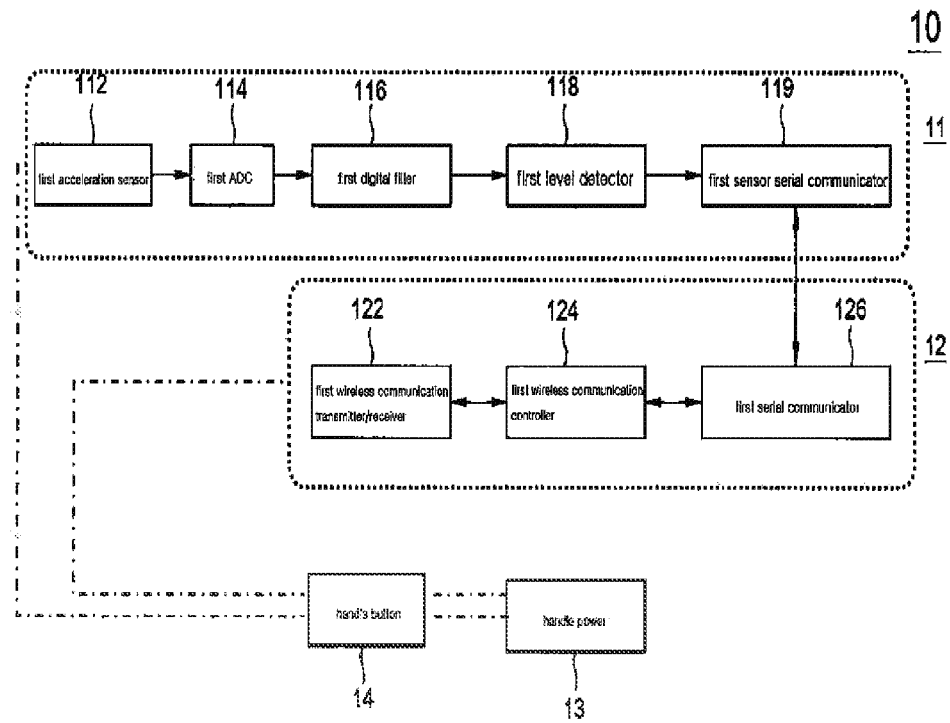
FIG. 2a is a detailed view of the constitution provided in a handle unit shown in FIG. 1, wherein an acceleration sensor module is used as a rotation sensing sensor module.

FIG. 2a is a detailed view of the constitution provided in the handle unit shown in FIG. 1, showing an example of using the acceleration sensor module as the rotation sensing sensor module.

As described above, the handle unit 10 includes the handle communication module 12 to transmit the data being output from the rotation sensing sensor module 11 (preferably, acceleration sensor module) and a first acceleration sensor 112 to wirelessly sense the movement of handles to the floor mat unit 20. When the acceleration sensor module 112 is used as the rotation sensing sensor module, it is preferable to install the acceleration sensor module 112 in the weight 15 extended from the handle to enable free rotation.

When the rotation sensing sensor module 11 is the acceleration sensor module as shown in FIG. 2a, it includes the first acceleration sensor 112, a first analog-digital converter 114, a first digital filter 116, a first level detector 118 and a first sensor serial communicator 119.

The first acceleration sensor 112 senses an acceleration of the three-dimensional space forming of an x-axis, y-axis and z-axis and outputs the direction and magnitude of the acceleration generated by the movement. The first acceleration sensor 112 outputs acceleration signals of the x-axis, y-axis and z-axis according to the movement of the handles, that is, the acceleration analog signal of the x-axis, the acceleration analog signal of the y-axis and the acceleration analog signal of the z-axis.

The first analog-digital converter (ADC) 114 samples the acceleration analog signal of the x-axis, the acceleration analog signal of the y-axis and the acceleration analog signal of the z-axis which are output from the first acceleration sensor 112 to be converted into the digital data. The acceleration data of the x-axis, acceleration data of the y-axis and acceleration data of the z-axis converted by the first analog-digital converter (ADC) 114 are provided to the first digital filter 116.

The first digital filter 116 performs filtering by using a predetermined band, to remove a noise or unnecessary vibration from the acceleration data of the x-axis, acceleration data of the y-axis and acceleration data of the z-axis which are converted by the first analog-digital converter (ADC) 114 and provided. The acceleration data of the x-axis, acceleration data of the y-axis and acceleration data of the z-axis filtered by the first digital filter 116 are provided to the first level detector 118.

The first level detector 118 detects levels corresponding to the handle motions of using the wireless and ropeless jump rope, by using the acceleration data of the x-axis, acceleration data of the y-axis and acceleration data of the z-axis which are filtered by the first digital filter 116 and provided. The first level detector 118 enables to output 1 when the acceleration data of two or more axes among the three axes is more than a predetermined critical value. The first level detector 118 also enables to output 1 when the acceleration data of each of the three axes is more than its relevant critical value. That is, the first level detector 118 outputs 1 if the acceleration data of the x-axis, acceleration data of the y-axis and acceleration data of the z-axis satisfy the predetermined critical values corresponding to the handle motions of the wireless and ropeless jump rope exercise. In the present invention, since the output only corresponding to the motions of the wireless and ropeless jump rope exercise detected by the first level detector 118 is transmitted as data, the amount of data to be transmitted is reduced and therefore it is possible to use Bluetooth in the embodiment.

The first level detector 118 further detects a case of forward-rotating the handles and a case of backward-rotating the handles. That is, the first level detector 118 further detects the motions of forwards and backwards, to be output.

The first sensor serial communicator 119 and a first serial communicator 126 are interfaces for the communication between the rotation sensing sensor module 11 and the handle communication module 12. The first sensor serial communicator 119 and the first serial communicator 126 may be I2C interfaces to be synchronized by a clock.

The handle communication module 12 includes the first serial communicator 126 as mentioned above, a first wireless communication controller 124 and a wireless communication transmitter/receiver 122.

The first wireless communication controller 124 controls the operations of the first serial communicator 126 and wireless communication transmitter/receiver 122. The first wireless communication controller 124 transmits the output of the rotation sensing sensor module 11 which is input in the first serial communicator 126 to the first wireless communication transmitter/receiver 122, to be transmitted to the mat communication module 23.

The wireless communication transmitter/receiver 122 is an interface to communicate with a second wireless communication transmitter/receiver 232 of the floor mat unit 20. To this end, the wireless communication transmitter/receiver 122 and the second wireless communication transmitter/receiver 232 may include a Bluetooth interface.

In the preferred embodiment of the present invention, the handle unit 10 may further comprise a handle power supply. The handle power supply provides the rotation sensing sensor module 11 and the handle communication module 12 with the power required for the operations. To this end, the handle power supply may include a battery. To prevent the power consumption of the battery, the handle unit 10 is switched to a sleep mode when the wireless and ropeless jump rope apparatus is not used.

In the preferred embodiment of the present invention, the handle unit 10 may further comprise a handle button 14. If needed, the handle button 14 can be used as a switch to supply/block the power required for the operations of the rotation sensing sensor module 11 and the handle communication module 12. In this case, the handle button 14 may be the constitution to sense the pressure of the handle(s).

Figure 2B:
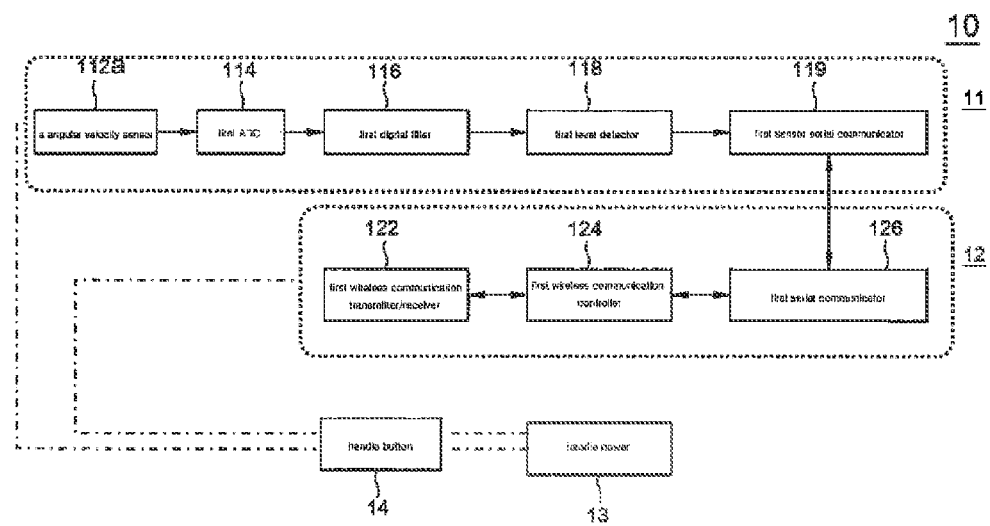
FIG. 2b is a detailed view of the constitution provided in a handle unit shown in FIG. 1, showing an example wherein an angular velocity sensor module is used as a rotation sensing sensor module.

FIG. 2b is a detailed view of the constitution provided in the handle unit shown in FIG. 1, showing another example of using the angular velocity sensor module as the rotation sensing sensor module. As shown in FIG. 2b, when the angular velocity sensor module is used as the rotation sensing sensor module 11, since the other constitution than the constitution of the angular velocity sensor module 112a instead of the acceleration sensor module 112 are the same as those in FIG. 2b, no description thereof will not be presented.

In the embodiment, the use of the acceleration sensor 112 or the angular sensor 112a as the rotation sensor module 11 has been described but the present invention is not limited thereto. It is possible to more accurately detect the rotations by using the combination of the acceleration sensor 112 and the angular sensor 112a. Further, the use of the acceleration sensor 112 or the angular sensor 112a as the rotation sensor module 11 in the embodiment has been described but the present invention is not limited thereto. It is possible to detect the rotations of the handle unit 10 of the wireless and ropeless jump rope of the user by using a photo interrupter sensor. In this case, a short string is connected to each handle of the handle unit 10, a shaft to rotate together with the string is positioned at each handle where the string is connected, and photo interrupt means like the blades of a fan are positioned between a light-emitting unit and a light-receiving unit. Therefore, the strings rotate as the user rotates the handles, the rotation shafts rotate as the strings rotate, and the photo interrupt means in the blade shape rotate between the light-emitting unit and the light-receiving unit as the rotation shafts rotate, so that the rotation of the handle unit of the user is sensed and the sensed rotation is wirelessly transmitted to the floor mat unit.

In the above description of the present invention, the acceleration sensor 112, the angular sensor 112a and the photo interrupt sensor are independently used as the rotation sensor module 11 but the present invention is not limited thereto. It is possible to use the combination(s) of the acceleration sensor, angular sensor and photo interrupt sensor.

In the exercise using an actual jump rope, the rope rotates by the rotation movements of the handle unit. At this time, an acceleration change and an angular velocity change occur simultaneously in the rotation motions of the handle unit. Therefore, to obtain a similar rotation motion effect to the jumping rope exercise, it is preferable to sense the acceleration and angular velocity of the handle unit including both of the acceleration sensor module and the angular velocity sensor module.

The handle unit 10 may further comprise an incline sensor (not shown). Preferably, the incline sensor is positioned at an upper end (which is in contact with the connection string 14) of the handle body 13 of the handle unit 10. Since the incline sensor senses the angle of incline of the handle unit 10, it contributes such that the user more correctly performs the exercise using the wireless and ropeless jump rope.

Figure 3:
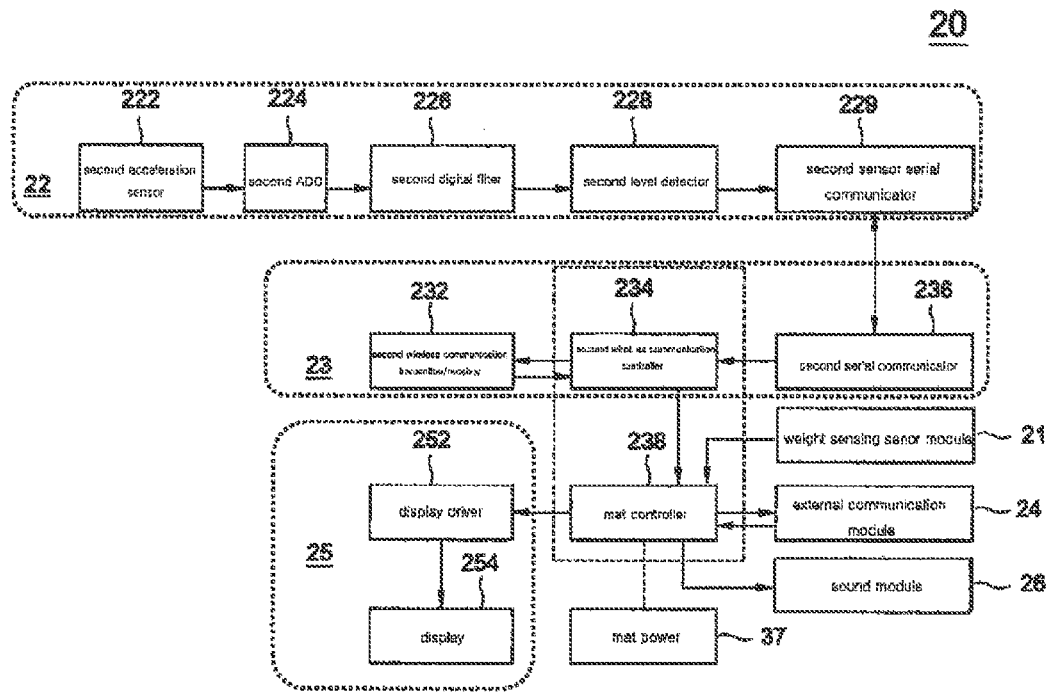
FIG. 3 is a detailed view of the constitution provided in a floor mat unit shown in FIG. 1.

FIG. 3 is a detailed view of the constitution provided in the floor mat unit shown in FIG. 1.

As described above, the floor mat unit 20 comprises the weight sensing sensor module 21 to measure the weight of the user, the jump sensing sensor module 22 to sense the jumps of the user, the mat communication module 23 to wirelessly receive the output of the rotation sensing sensor module 11 from the handle communication module 12 and to synchronize the output of the rotation sensing sensor module 11 and the output of the jump sensing sensor module 22, to count the number of jumps with the wireless and ropeless jump rope, and the external communication unit 24 to transmit data of the number of jumps with the wireless and ropeless jump rope and the weight of the user to the health promotion server 30 positioned at the external network and to receive any necessary information data from the health promotion server 30. The floor mat unit 20 may further comprise the display module 25 to visually display the weight of the user and the number of jumps with the wireless and ropeless jump rope to be informed to the user and the sound module 26 to provide sound, such as simple precautions or guidance or a start alarm before the user starts the exercise using the wireless and ropeless jump rope or to provide audibly an end alarm and a guide voice such as an end guidance after the user finishes.

The weight sensing sensor module 21 is to measure the weight of the user. The weight sensing sensor module 21 includes a digital scale or analog scale and the mode of the scale is not limited. For example, to measure the weight of the user, it is possible to measure the weight by using a spring or a load cell with a metal having elasticity. In the case of using the load cell, when a pressure is applied, the metal having elasticity generates a change and electricity is applied to the changing metal. As the metal changes, it is compared with the metal before it was changed. The weight is measured by measuring the amount of the pressure as applied by measuring how much the electric resistance increases by using the property which is not electrically charged. The data on the weight of the user measured by the weight sensing sensor module 21 is transmitted to a mat controller 238.

The jump sensing sensor module 22 may comprise a switch (not shown) operating if a load is applied on the mat. The switch may use the currently publicly known techniques, such as a tape switch mode, a bumper switch mode, a contact switch mode, an acceleration switch mode and a laser switch mode. In the embodiment, for example, the acceleration sensor is used as the jump sensing sensor module 22 but the present invention is not limited thereto.

The jumping sensing sensor module 22 includes a second acceleration sensor 222, a second analog-digital converter 224, a second digital filter 226, a second level detector 228 and a second sensor serial communicator 229.

The second acceleration sensor 222 senses an acceleration of the three-dimensional space forming of an x-axis, y-axis and z-axis and outputs the direction and magnitude of the acceleration generated by the movement. The first acceleration sensor 112 outputs acceleration signals of the x-axis, y-axis and z-axis according to the motions of the handles, that is, the acceleration analog signal of the x-axis, the acceleration analog signal of the y-axis and the acceleration analog signal of the z-axis.

The second analog-digital converter (ADC) 224 samples the acceleration analog signal of the x-axis, the acceleration analog signal of the y-axis and the acceleration analog signal of the z-axis which are output from the second acceleration sensor 222, to be converted into digital data. The acceleration data of the x-axis, acceleration data of the y-axis and acceleration data of the z-axis converted by the second analog-digital converter (ADC) 224 are provided to the second digital filter 226.

The second digital filter 226 performs filtering by using a predetermined band, to remove a noise or unnecessary vibration from the acceleration data of the x-axis, acceleration data of the y-axis and acceleration data of the z-axis which are converted by the second analog-digital converter (ADC) 224 and provided. The acceleration data of the x-axis, acceleration data of the y-axis and acceleration data of the z-axis filtered by the second digital filter 226 are provided to the second level detector 228.

The second level detector 228 detects levels corresponding to the jumps with the wireless and ropeless jump rope, by using the acceleration data of the x-axis, acceleration data of the y-axis and acceleration data of the z-axis filtered by the second digital filter 226 and provided. The second level detector 228 enables to output 1 when the acceleration data of one or more axes among the three axes is more than a predetermined critical value. The second level detector 228 also enables to output 1 when the acceleration data of each of the three axes is more than its relevant critical value. That is, the second level detector 228 outputs 1 if the acceleration data of the x-axis, acceleration data of the y-axis and acceleration data of the z-axis satisfy the predetermined critical values corresponding to the jumps made using the wireless and ropeless jump rope.

The second sensor serial communicator 229 and a second serial communicator 236 are interfaces for the communication between the jump sensing sensor module 22 and the mat communication module 23. The second sensor serial communicator 229 and the second serial communicator 236 may be I2C interfaces to be synchronized by a clock.

A second wireless communication controller 234 controls the operations of the second serial communicator 236 and the second wireless communication transmitter/receiver 232. The second wireless communication controller 234 provides the output of the jump sensing sensor module 22 being input in the second serial communicator 236 to the mat controller 238.

The second wireless communication transmitter/receiver 232 is an interface to communicate with the first wireless communication transmitter/receiver 122 of the handle unit 10. The output of the first acceleration sensor 112 received in the second wireless communication transmitter/receiver 232 is provided to the mat controller 238 through the second wireless communication controller 234.

The mat controller 238 synchronizes the output of the rotation sensing sensor module 11 and the output of the jump sensing sensor module 22. The mat controller 238 checks whether the output of the rotation sensing sensor module 11, which is received in a pulse cycle where the output of the jump sensing sensor module 22 corresponds to a jump, is 1.

When the output of the jump sensing sensor module 22 corresponds to a jump and the output of the rotation sensing sensor module 11 as received is 1, the mat controller 238 determines that the user has completed the wireless and ropeless jump rope exercise and increases the number of counts of jumping the wireless and ropeless jump rope.

During the pulse cycle where the output of the jump sensing sensor module 22 corresponds to the jump, the mat controller 238 further determines how many times the output, 1, of the rotation sensing sensor module 11 as received has been input, to count a double under or triple under.

The mat controller 238 further checks whether the output of the jump sensing sensor module 22 corresponds to a jump and simultaneously the direction of the output of the rotation sensing sensor module 11 as received is forward or backward, to distinguish a forward jump and a backward jump.

Further, when the jump sensing sensor module 22 detects no jump of the user for a predetermined time or the user comes down from the floor mat unit 20, the mat controller 238 determines that the user has stopped the wireless and ropeless jump rope exercise, to determine the time of the wireless and ropeless jump rope exercise, from the point that the user starts the exercise using the wireless and ropeless jump rope to the point that the last jump is performed, and to count the time.

In FIG. 3, the second wireless communication controller 234 and the mat controller 238 are distinguishably described but these are actually processed as one MICOM only. Therefore, the second wireless communication controller 234 and the mat controller 238 can be processed in a single MICOM. Since one MICOM is able to perform the functions of both of the second wireless communication controller 234 and the mat controller 238, it prevents an increase in cost.

As described above, the external communication module 24 is configured to transmit a value of counting the number of jumps with the wireless and ropeless jump rope and the time of the wireless and ropeless jump rope exercise measured in the mat controller 238 of the mat communication module 23 to the health promotion server 30 positioned at the external network, such that the data received from the health promotion server 30 is received through the mat controller 238 and is output through the display module 2 or sound module 26.

Although the external communication module 24 may use any one of a wire communication module and a wireless communication module compatible with the Ethernet, the embodiment uses the wireless communication module using Wi-Fi for the mobility and convenience of the wireless and ropeless jump rope apparatus.

Figure 4:
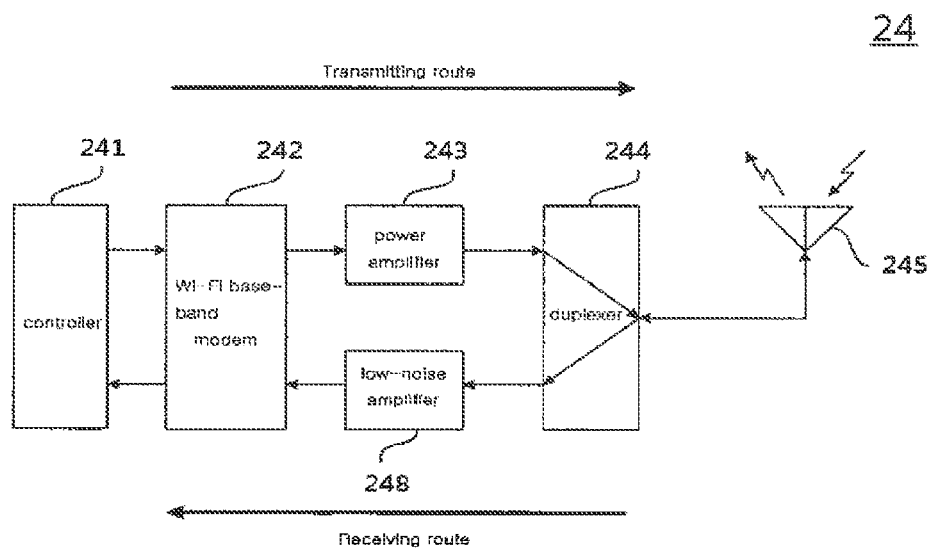
FIG. 4 is a block diagram to schematically explain a transmitting/receiving function of an external communication module according to the present invention.

FIG. 4 is a block diagram to schematically explain a transmitting/receiving function of the external communication module 24 according to the present invention. The function of the Wi-Fi wireless WLAN enables for each terminal (herein, the floor mat unit) to access the Internet through a wireless router. Referring to FIG. 4, the Wi-Fi module used as the external communication module 24 includes a Wi-Fi controller 241, a Wi-Fi baseband modem 240, a power amplifier 243, a low-noise amplifier 248, a duplexer 244 and an antenna 245.

A general transmitting/receiving route by the Wi-Fi module will be briefly described herein. In the transmitting route, the WIFI controller 241 modulates the data received from the mat controller 238 through the baseband modem 242, to generate a Wi-Fi digital signal. When the Wi-Fi digital signal is converted into an analog signal to be input in the power amplifier 243, the power is amplified through the power amplifier 243 and the signal is transmitted to the antenna 245 through the duplexer 244 and transmitted to the external network through the surrounding AP (not shown).

On the contrary to this, the receiving route will be described in order. When an RF signal in an analog form the health promotion server 30 received from the antenna 245 is input into the low-noise amplifier 248 through the duplexer 244, the low-noise amplifier 248 controls noise and amplifies the signal. The RF signal is converted into a digital signal to be sent to the Wi-Fi baseband modem 242 and the Wi-Fi baseband modem 242 generates digital data by demodulating the received RF signal. After that, the digital data is sent to the Wi-Fi controller 241 and the Wi-Fi controller 241 transmits the data to the mat controller 238 through a data bus, thereby establishing the communication between the external health promotion server 30 and the mat controller 238.

As described above, the floor mat unit 20 according to the present invention includes the external communication module 24 to support two directions for the communication with the outside. Therefore, it is possible to transmit the data, such as the number of jumps the user makes and the time of the wireless and ropeless jump rope exercise, to the external health promotion server 30 and it is also possible to receive the data from the health promotion server 30 and to output the data through the display module 25 or sound module 26 to be described later. For example, when the user positions on the floor mat unit 20, the weight of the user is transmitted to the external health promotion server 30 according to the above-stated route. The health promotion server 30 compares the weight of the user saved in its database and the current weight of the user and transmits the result in the form of data in voice or text to the relevant floor mat unit 20. The floor mat unit 20 is able to notify the user of the data in voice or text through the sound module 25 or display module 25.

According to the present invention, the floor mat unit 20 further comprises the display module 25. The display module 25 is realized as the LCD on the floor mat unit 20 and includes a display driver 252 and a display 254. The display driver 252 displays the number of jumps with the wireless and ropeless jump rope, the amount of consumed calories and the text message from the health promotion server 30 on the display 254. The number of jumps with the wireless and ropeless jump rope or the time of the wireless and ropeless jump rope exercise is displayed on the display 254 by the driving of the display driver 252.

Furthermore, as shown in FIG. 3, the floor mat unit 20 of the present invention may further comprise the sound module 26 to provide a voice guide to the user. The sound module 26 outputs to the user the voice guide stored in the floor mat unit 20 or the data in voice transmitted from the health promotion server 30.

A mat power source 37 provides the power needed for the operations of the weight sensing sensor module 21, jump sensing sensor module 22, mat communication module 23, external communication module 24, display module 25 and sound module 26.

If the wireless and ropeless jump rope apparatus is not used, the weight sensing sensor module 21, jump sensing sensor module 22, mat communication module 23, external communication module 24, display module 25 and sound module 26 can be switched to the sleep mode. In this case, if any load is sensed in the weight sensing sensor module 21 or 1 is output from the jump sensing sensor module 22 during the sleep mode, these can return to a normal operation mode.

Figure 5:
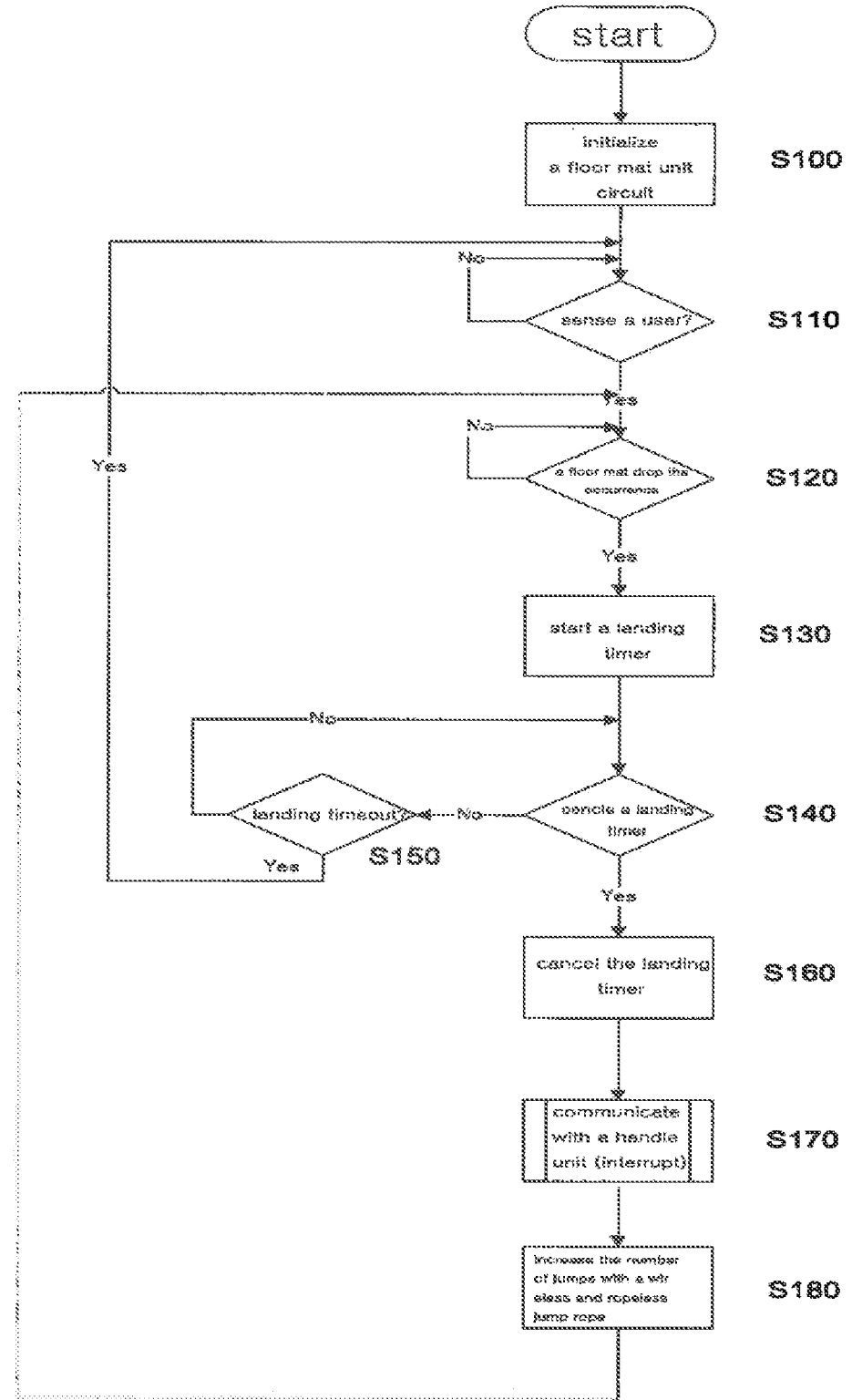
FIG. 5 is a flow chart illustrating a process of the floor mat unit according to the embodiment of the present invention.

FIG. 5 is a flow chart illustrating a process of the floor mat unit 20 according to the embodiment of the present invention.

As shown in FIG. 5, in step S100, the mat controller 238 of the floor mat unit 20 initializes a circuit of the floor mat unit 20 before the wireless and ropeless jump rope exercise starts. This initialization is performed when the user turns on the power of the floor mat unit 20.

After the floor mat unit 20 is initialized, in step S110, the mat controller 238 senses whether the user is positioned on the mat, based on the value transmitted from the jump sensing sensor module 22. When it senses that the user is positioned on the mat, in step S120, the mat controller 238 senses a jump of the user on the mat.

In step S120, if no jump is performed by the user (if no impact occurs at a foot indication position), the mat controller 238 waits until the user jumps and if the user jumps (if the impact is sensed at the foot indication position), it proceeds to step S130.

In step S130, the mat controller 238 operates a landing timer, to distinguish the user's jump action from his/her action of completely stepping out from the foot indication position. In step S140, if the user's feet are sensed on the mat, the mat controller 238 determines whether the user's action of pressurizing the foot indication position has occurred on the mat, based on the time of the landing timer.

If the foot indication position is pressurized by the user's feet within a preset time of the landing timer, the mat controller 238 determines that the user has jumped and it proceeds to step S160. In step S160, the mat controller 238 ignores the landing timer has been set in step S130, however, if the foot indication position is not pressurized, it proceeds to step S150. If the time at which the landing timer starts is within the range being preset in the landing timer, it returns to step S140. If the time at which the landing timer starts is not within the range being preset in the landing timer, the mat controller 238 determines that the user stepped out from the foot indication position and it returns to step S110.

If the foot indication position is pressurized within the normal jumping time range in step S140, the landing timer is off in step S160. After that, in step S170, the mat controller 238 transmits an interrupt command instructing the handle unit 10 to send the rotation information. In step S180, the number of jumps made by the user of the wireless and ropeless jump rope is counted based on the rotation information transmitted from the handle unit 10 and it returns to step S120 to sense the next jump of the user.

Figure 7:
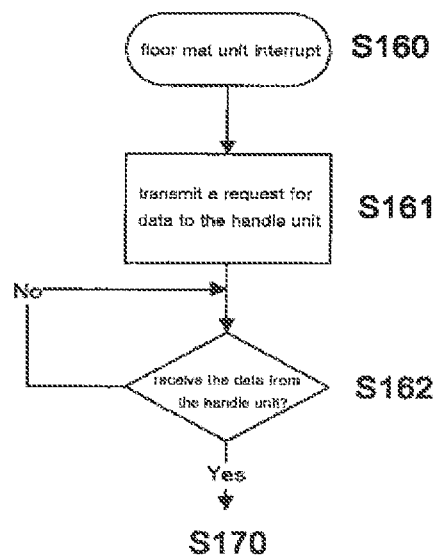
FIG. 7 is a flow chart illustrating an interrupt process of the floor mat unit.

FIG. 7 shows the process of the interrupt command generated from the mat controller 238 of the floor mat unit 20 to the handle unit 10 in step S160. If the user's pressure at the foot indication position is sensed in step S140, the mat controller 238 requests the handle unit 10 to send the rotation information (rotation data) in step S161 and receives the data from the handle unit 10 in step S162, thereby counting the number of jumps with the wireless and ropeless jump rope, based on the received data.

Figure 6:
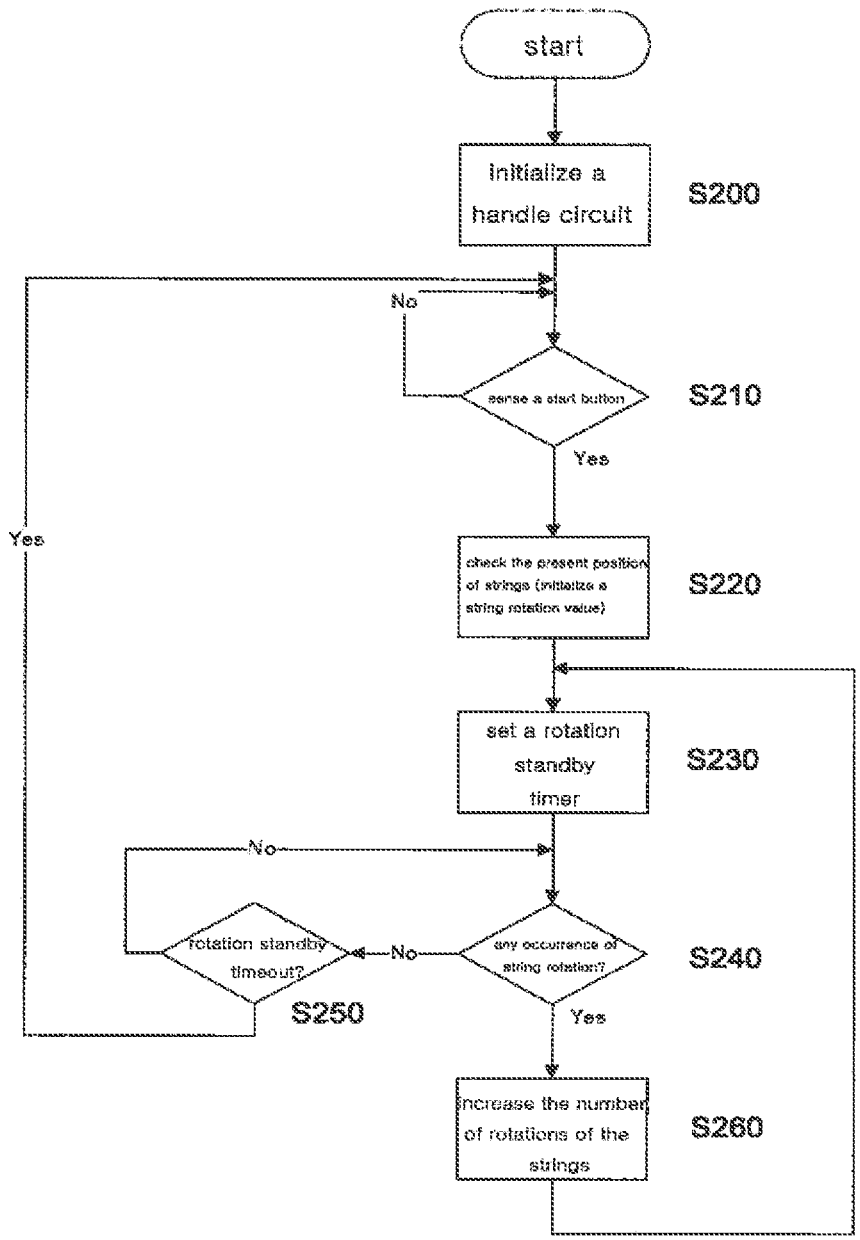
FIG. 6 is a flow chart illustrating a process of the handle unit according to the embodiment of the present invention.

FIG. 6 is a flow chart illustrating a process of the handle unit 10 according to the embodiment of the present invention.

As shown in FIG. 6, in step S200, the handle unit 10 initializes a circuit of the handle unit 10 before the user starts the wireless and ropeless jump rope exercise. This initialization is performed by the user's turning on the power of the handle unit 10.

After the initialization is performed, if the user turns on a start button in step S210, the rotation sensing sensor module 11 checks for the current position of the string(s) (that is, a current position value of the rotation sensing sensor) in step S220 and a rotation standby timer starts in step S230.

Like the landing timer described above, the rotation standby timer is used to determine whether the user completes the rotation within a normal range or the user stops the wireless and ropeless jump rope exercise. That is, if a rotation occurs within the range of a value which is set in the rotation standby timer, the user's rotation is determined as being completed in step S240 and the number of string rotations is counted in step S260.

However, if no string rotation occurs in step S240, whether a rotation standby time is within the range of a predetermined critical value is determined in step S250. If the rotation standby time is within the range of the critical value, returning to step S240, the rotation standby timer waits for the occurrence of the string rotation. If the rotation standby time is not within the range of the predetermined critical value in step S250, it is determined that the user put down the handle unit 10 or stopped the wireless and ropeless jump rope exercise and then it returns to step S210.

Figure 8:
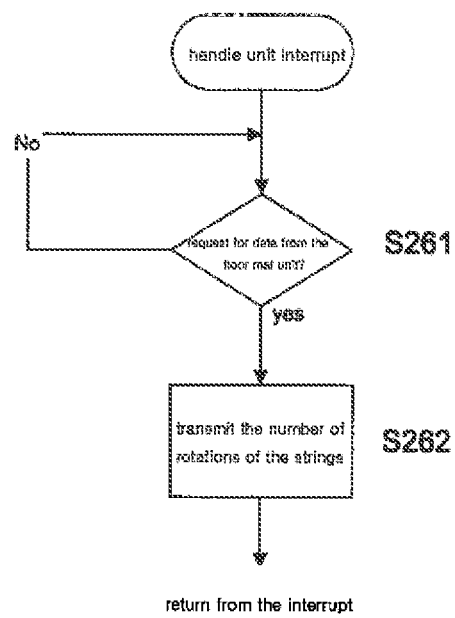
FIG. 8 is a flow chart illustrating an interrupt process of the handle unit.

FIG. 8 is a flow chart illustrating an interrupt process of the handle unit 10. In the floor mat unit 20, the request for interrupt is regularly generated to the handle unit 10 after the mat is pressured. However, the handle unit 10 is configured to respond to the request for interrupt from the floor mat unit 20 immediately after receiving the request for interrupt.

Therefore, as in step S262, if the handle unit 10 receives the request for data from the floor mat unit 20, it transmits a count value of the string rotations and then it returns to the step before the request for interrupt.

Figure 9:
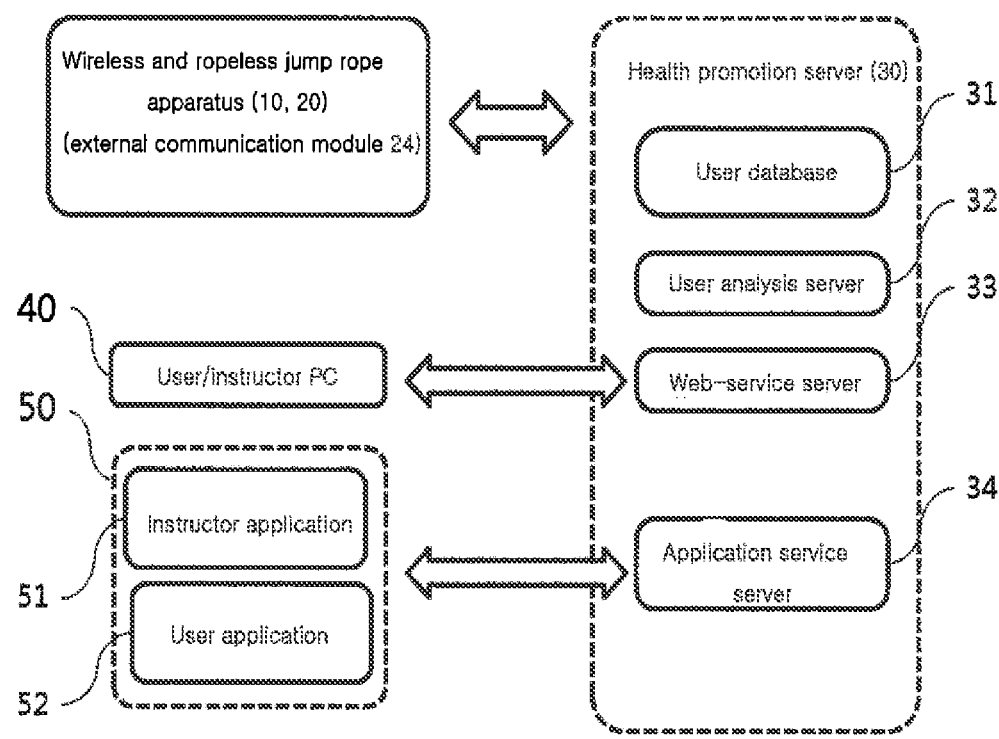
FIG. 9 is a view of the health promotion system according to the present invention, comprising the wireless and ropeless jump rope apparatus, the health promotion server and the user terminal.

FIG. 9 is a view of the health promotion system comprising the wireless and ropeless jump rope apparatus with the handle unit 10 and the floor mat unit 20, the health promotion server 30 and user terminals 40, 50 according to the present invention.

Since the wireless and ropeless jump rope apparatus with the handle unit 10 and the floor mat unit 20 has been fully described with reference to FIG. 1 through FIG. 8, no further description will be presented. Hereinafter, the mutual operations of the wireless and ropeless jump rope apparatus with the handle unit 10 and the floor mat unit 20, health promotion server 30 and user terminals 40, 50 will be specifically described.

The health promotion server 30 comprises a user database 31, a user analysis server 32, a web-service server 33 and an application service server 34. The user database 31 records and stores the information of the individual user and the information of the wireless and ropeless jump rope apparatus, specifically, the number of jumps the user makes and the time of the wireless and ropeless jump rope exercise transmitted from the floor mat unit 20. The user analysis server 32 is to generate user analysis data or materials by analyzing the user's level of the wireless and ropeless jump rope exercise and health conditions, based on the information from the user database. The web-service server 33 is to provide the analysis data to the user/instructor PC 40 connected to the webpage of the health promotion server 30, based on the user analysis data from the user analysis server 32. The application service server 34 is to be provided to the user through an application 50 performed on a smart phone, preferably an instructor application 51 or a user application 52, based on the user analysis data.

The user database 31 stores the individual user information, the user's wireless and ropeless jump rope exercise history and the analysis data analyzed in the user analysis server 32. The individual user information is stored in the user database if the user connects to the webpage of the health promotion server 30 through the internet and fills in a prescribed input form. If the user is a student, the individual information to be stored includes a name, school, grade, class, sex, age, height, weight and photo. Specially, the information, such as age, height and weight, is used as the factor to analyze the health conditions of the individual user in the user analysis server 32 to be described below.

The user analysis server 32 of the health promotion server 30 generates analysis data of the wireless and ropeless jump rope exercise, health analysis data, and recommended health data of the individual user, by using the original input information of the user, such as age, height and weight saved in the user database 31, the information of the wireless and ropeless jump rope exercise performed in past (the number of jumps the user makes and the time of the wireless and ropeless jump rope exercise), and the currently transmitted information of the wireless and ropeless jump rope exercise (the number of jumps the user makes and the time of the wireless and ropeless jump rope exercise).

The analysis data of the wireless and ropeless jump rope exercise provides a trend in the user's wireless and ropeless jump rope exercise from the past to the present, the amount of the exercise thereof by day/month, the average number of successful jumps with the wireless and ropeless jump rope per use, the maximum number of successful jumps with the wireless and ropeless jump rope per use, the maximum duration of using the wireless and ropeless jump rope per use, the average/maximum/minimum number of jumps with the wireless and ropeless jump rope per minute, the analysis data on consumed calories and the relevant statistical data. The analysis data of the wireless and ropeless jump rope exercise can be provided regarding each of the forwards, double unders and backwards.

The health analysis data analyzes whether the user is overweight, low-weight or low-physical strength, based on the analysis data of the wireless and ropeless jump rope exercise and the weight information of the user. The health analysis data also performs an intensive analysis of whether the user is good or weak in regard to the necessary elements of the wireless and ropeless jump rope exercise, such as endurance, reflex, etc.

To strengthen the weak element of the user based on the health analysis data of the individual user, the recommended health data generates data relating to the recommended amount of exercise per day, recommended diet and recommended exercise and provides the relevant data to the user to improve the user's health.

The web-service server 33 enables for the user or instructor to be provided, through the PC, the service offered from the homepage of the health promotion server 30. The web-service server 33 makes it possible for the user or instructor who does not use a smart phone to be provided with the service of the health promotion server 30 through its web-based service.

Preferably, the service provided from the web-service server 33 may vary according to the authority given to the user as described above.

When the user is a student, (s)he can view, through the web-service server 33, the statistical data, such as her/his individual information, the analysis data and statistical data of her/his wireless and ropeless jump rope exercise, for example, the total/recent number of jumps with the wireless and ropeless jump rope performed by her/him, the average/maximum/minimum number of successful jumps with the wireless and ropeless jump rope per use, the average/maximum/minimum number of jumps with the wireless and ropeless jump rope per minute, and the total/recent amount of consumed calories.

Through the web-service server 33, a teacher can be provided with the analysis data by the data mining, such as approval data when a student member joins, wireless and ropeless jump rope data of each student, wireless and ropeless jump rope data of the total of students, wireless and ropeless jump rope data by classes. A data mining tool may be further provided for an in-depth analysis. In addition, a function of exchanging the wireless and ropeless jump rope data among teachers and a function of administrating a contest related to a wireless and ropeless jump rope contest may be further provided. A teacher may be further provided with the health analysis data and the recommended health data as described above.

Like the teacher's case, the parents can be provided with the analysis data of a student's wireless and ropeless jump rope exercise, the health analysis data and the recommend health data through the web-service server 33.

The application service server 34 provides the user or instructor using a smart phone with the service provided from the health promotion server 30. The user or instructor downloads a proper application to her/his smart phone from an application market (the Android-based smart phone downloads the relevant application from the Goggle market and the iPhone OS downloads the relevant application from the Apple store).

After the user or instructor executes the application as downloaded and gets certification through the ID registered in the user database, (s)he can be provided with the service from the application service server 34.

When the user is a student, (s)he can receive her/his wireless and ropeless jump rope exercise information in her/his smart phone, by pairing the Bluetooth function of the smart phone and the Bluetooth function which is the mat communication module 23 installed in the floor mat unit 20 through the application installed in the smart phone.

As described above, in the present invention, after the mat controller 238 transmits the exercise information to the health promotion server 30 and after the exercise information is saved in the health promotion server 30, the user can receive the information of the wireless and ropeless jump rope exercise performed by her/him through the application service server 34. Transmitting/receiving the data through a smart phone is possible in real-time for the communication with the health promotion server 30, through any means of a 3G communication module, a 4G communication module and Wi-Fi module installed in the smart phone.

Through a student application installed in the smart phone, a student can view, through the application service server 33, her/his individual information and the analysis data of the wireless and ropeless jump rope exercise, such as the statistical data of the wireless and ropeless jump rope exercise performed by her/him, the analysis data and the amount of consumed calories, which are provided from the user analysis server 32.

Through the instructor application 51 installed in the smart phone, a teacher can be provided with the analysis data by the data mining, such as approval data when a student member joins, wireless and ropeless jump rope data of each student, wireless and ropeless jump rope data of the total of students, wireless and ropeless jump rope data by classes. A data mining tool may be further provided for an in-depth analysis. In addition, a function of exchanging the wireless and ropeless jump rope data among teachers and a function of administrating a contest related to a wireless and ropeless jump rope contest may be further provided. A teacher may be further provided with the health analysis data and the recommended health data as described above.

Like the teacher's case, the parents can be provided with the analysis data of the wireless and ropeless jump rope exercise, the health analysis data and the recommend data for health of the relevant student, through the instructor application 51 installed in the smart phones.

(Example for Operating the Health Promotion System Using the Wireless and Ropeless Jump Rope Apparatus in a School)

The case where the wireless and ropeless jump rope apparatus according to the present invention is installed in a school will be described. In this case, since the handle unit 10 of the wireless and ropeless jump rope apparatus does not need any physical string, it is possible to install the wireless and ropeless jump rope apparatus in a small space like an empty classroom.

The handle unit 10 with a pair of handles and the floor mat unit 20 of the wireless and ropeless jump rope apparatus are installed in the place like the empty classroom.

When a user starts exercise by using the wireless and ropeless jump rope apparatus, basic registration information of a student(s) and a teacher needs to be input in advance in the health promotion server 30. Preferably, the wireless and ropeless jump rope apparatus to be used by a student may be arranged in advance per student. The teacher checks whether any student is absent or there is any vacancy by class before starting the exercise. It is also preferable for the teacher to check whether the wireless and ropeless jump rope apparatus is properly assigned to the relevant student. When a plurality of the wireless and ropeless jump rope apparatuses are installed in the classroom, for example, a total of twenty (20) wireless and ropeless jump rope apparatuses numbered from 1 to 20 are installed, a first wireless and ropeless jump rope apparatus may be assigned to a first student, a second wireless and ropeless jump rope apparatus to a second student, and a $N^{th}$ wireless and ropeless jump rope apparatus to a $N^{th}$ student.

However, if the wireless and ropeless jump rope apparatus has an identification function, the process of checking whether the wireless and ropeless jump rope apparatus is properly assigned to the relevant student may be omitted. For the automatic identification of the student in the wireless and ropeless jump rope apparatus, a special RFID tag may be provided to the student and a RFID tag reading module may be additionally installed in the floor mat unit 20. Or a particular barcode may be given to each user when a student registers in the health promotion server 30 and a barcode reading module may be additionally installed in the floor mat unit 20. The information identified from a user identification module is transmitted to the health promotion server 30, together with the information on the number of jumps the user makes using the wireless and ropeless jump rope and the time of the wireless and ropeless jump rope exercise.

The teacher confirms whether the relevant student matches with the relevant wireless and ropeless jump rope apparatus through the screen of the smart phone. To check whether anyone attends as a substitute, the teacher may further confirm the picture included in the individual information of each student, through the application installed in the smart phone.

After the teacher finishes confirming the matching of the student and wireless and ropeless jump rope apparatus and checking the attendance of students, the teacher proceeds with the wireless and ropeless jump rope class by pressing the start button installed in her/his smart phone.

When each student is positioned on the floor mat unit 20 of the relevant wireless and ropeless jump rope apparatus, the weight sensing sensor module 21 installed in the floor mat unit 20 measures the weight of the student which is the user and transmits the measured weight to the mat controller 238. When the mat controller 238 receives the student's weight, it transmits it to the external health promotion server 30 and the health promotion server 30 records the user's current weight in the user database 31.

When each student carries out the wireless and ropeless jump rope in the wireless and ropeless jump rope apparatus assigned to her/him, the mat controller 238 of the floor mat unit 20 calculates the number of jumps the user makes with the wireless and ropeless jump rope and the time of the wireless and ropeless jump rope exercise and transmits the relevant data to the health promotion server 30. The health promotion server 30, specifically the user analysis server 32 of the health promotion server 30, records the number of jumps the user makes and the time of the wireless and ropeless jump rope exercise in the user database 31 and transmits the results of the wireless and ropeless jump rope exercise currently performed by the user to the instructor application 51 installed in the smart phone of the teacher. Based on the recent weight of the user and the number of jumps the user makes and the time of the wireless and ropeless jump rope exercise, the user analysis server 32 performs various analyses, such as the analysis on whether the relevant student is overweight/low physical strength, analysis of diet and exercise, analysis of individually recommended diet, analysis of a trend in the wireless and ropeless jump rope exercise of the student and analysis of wireless and ropeless jump rope data mining and transmits the results of the analyses to the application of the smart phone of each student, the teacher and the parents, selectively.

According to the present invention, even if one teacher is in charge of a number of students, the teacher does not need to count the number of jumps each student makes from start to end. Therefore, the teacher can assign much more time to student guidance for using the wireless and ropeless jump rope. Furthermore, since the teacher can easily know the weight state, the change or development in the wireless and ropeless jump rope exercise and whether overweight/low strength of each student, based on the analysis data (materials) provided from the health promotion server, a customized health promotion result for each student is possible.

Further, according to the present invention, since the wireless and ropeless jump rope apparatus does not need any physical rope, using the wireless and ropeless jump rope can be conducted in a small-sized indoor area such as an empty classroom. Therefore, even in the school where there is no indoor gym or indoor auditorium hall, the wireless and ropeless jump rope exercise can be easily conducted without any outside weather influence (for example, snow, rain, yellow dust, fine dust and toxic gas).

Further, according to the present invention, since a data mining analysis and statistical analysis are possible without any time investment, based on the data of jumps each student makes by using the wireless and ropeless jump rope, it is possible to encourage the wireless and ropeless jump rope exercise by offering an incentive (by providing a book gift, gift certificate or gift card) to a top-ranking school or student.

Further, according to the present invention, since the state of the physical strength of each student or the recommended amount of exercise and recommended diet information corresponding to the physical strength state are provided from the health promotion server to the teacher or parents, the efficiency of the physical strength and health promotion of the student is improved.

The invention has been described using preferred exemplary embodiments. However, it is to be understood that the scope of the invention is not limited to the disclosed embodiments. On the contrary, the scope of the invention is intended to include various modifications and alternative arrangements within the capabilities of persons skilled in the art using presently known or future technologies and equivalents.

The scope of the claims, therefore, should be accorded the broadest interpretation so as to encompass all such modifications and similar arrangements.

What is claimed is:

1. A health promotion system using a wireless and ropeless jump rope comprising: a wireless and ropeless jump rope apparatus with a handle unit and a floor mat unit, a health promotion server configured to communicate with the wireless and ropeless jump rope apparatus, and a user terminal to access the health promotion server, the handle unit comprising:
  a pair of handle bodies, where each handle body has a weight and a string where the string connects the handle body to the weight,
  an acceleration sensor and an angular velocity sensor included in the weight as a rotation sensing sensor module to sense the rotation of the weight of each handle body,
  an incline sensor further installed in an upper end of the handle body where the string is fixed, to detect an incline of the handle unit, and
  a handle communication module to transmit an output of the rotation sensing sensor module and an output of the incline sensor to the floor mat unit, the floor mat unit comprising:
  a weight sensing sensor module to sense a user's current weight when the user is positioned on the floor mat unit,
  a jump sensing sensor module to sense the user's jumps when the user jumps on the floor mat unit,
  a mat communication module to receive the output of the rotation sensing sensor module and the output of the incline sensor transmitted from the handle communication module
  a mat controller to count a number of jumps made by the user of the wireless and ropeless jump rope, by using the outputs of the rotation sensing sensor module and incline sensor received through the mat communication module and the output of the jump sensing sensor module of the floor mat unit, and
  an external communication module to transmit the user's weight measured in the weight sensing sensor module and the number of the jumps counted in the mat controller, and the health promotion server comprising:
  a user database to store information including the user's height and an initial weight input when the user registers in the health promotion server and the user's current weight, the number of jumps made by the user of the wireless and ropeless jump rope and the amount of time using the wireless and ropeless jump rope which are transmitted from the external communication module of the wireless and ropeless jump rope apparatus,
  a user analysis server to analyze the information stored in the user data base and to store the analyzed data in the user database,
  a web-service server, and
  an application service server to provide the data analyzed in the user analysis server through an application installed in the user terminal, wherein the user analysis server generates analysis data of the user's wireless and ropeless jump rope exercise, by using the height and the initial weight information stored in the user database the user's current weight, the number of jumps made by the user of the wireless and ropeless jump rope and the amount of time using the wireless and ropeless jump rope as transmitted from the external communication module of the wireless and ropeless jump rope apparatus, and the user analysis server provides the generated analysis data to the user terminal.

2. The health promotion system using the wireless and ropeless jump rope apparatus of claim 1, wherein the user analysis server further provides health analysis data and recommended health data of the user, by using the height and the initial weight information stored in the user database, the user's current weight, the number of jumps made by the user of the wireless and ropeless jump rope and the amount of time using the wireless and ropeless jump rope as transmitted from the wireless and ropeless jump rope apparatus.

3. The health promotion system using the wireless and ropeless jump rope apparatus of claim 2, wherein the application installed in the user terminal includes a student application and an instructor application and if the application installed the user's application is the student application, the data analyzed in the user analysis server and provided to the user is analysis data of the wireless and ropeless jump rope exercise and if the application is the instructor application, the health analysis data and recommended health data are provided in addition to the analysis data of the wireless and ropeless jump rope exercise.

4. The health promotion system using the wireless and ropeless jump rope apparatus of claim 3, wherein the analysis data of the wireless and ropeless jump rope exercise is a trend in the user's wireless and ropeless jump rope exercise from a past point to a present point, an amount of exercise by day or month or combination thereof, an average number of successful jumps with the wireless and ropeless jump rope per use, a maximum number of successful jumps with the wireless and ropeless jump rope per use, a maximum duration of using the wireless and ropeless jump rope per use, an average, a maximum, a minimum, or a combination thereof, number of jumps with the wireless and ropeless jump rope per minute, consumed calories per day or month or combination thereof, and the statistical data on the exercise using the wireless and ropeless jump rope.

5. The health promotion system using the wireless and ropeless jump rope apparatus of claim 4, wherein the health analysis data includes the analysis data of the wireless and ropeless jump rope exercise, the data analyzing whether the user is overweight, low-weight or low-physical strength by comparing the user's height and initial weight information with the amount of the wireless and ropeless jump rope exercise, and evaluation data of the user's elements required for the wireless and ropeless jump rope exercise.

6. The health promotion system using the wireless and ropeless jump rope apparatus of claim 1, wherein the jump sensing sensor module uses any one of a tape switch mode, a bumper switch mode, a contact switch mode, an acceleration switch mode and a laser switch mode.

7. The health promotion system using the wireless and ropeless jump rope apparatus of claim 6, wherein the mat controller changes the wireless and ropeless jump rope apparatus from a sleep mode to a normal operation mode if the operation of the switch is sensed.

8. The health promotion system using the wireless and ropeless jump rope apparatus of claim 1, wherein the recommended health data is the data relating to the recommended amount of exercise, recommended diet and recommended exercise which are customized for the user, to strengthen a weak element of the user based on the health analysis data of the user.

* * * * *